US00PP11230P

United States Patent [19]

Martin

[11] Patent Number: Plant 11,230

[45] Date of Patent: Feb. 22, 2000

[54] FERN PLANT NAMED 'LAUA'E IKI'

[76] Inventor: Robert T Martin, P.O. Box 400, Paia, Hi. 96779

[21] Appl. No.: 08/975,373

[22] Filed: Nov. 20, 1997

[51] Int. Cl.[7] ..... A01H 5/00

[52] U.S. Cl. ..... Plt./379

[58] Field of Search ..... Plt./88.3, 379

[56] References Cited

U.S. PATENT DOCUMENTS

P.P. 9,238 8/1995 Tas ..... Plt./88.3

OTHER PUBLICATIONS

The New Royal Horticultural Society Dictionary of Gardening, Editor–in–Chief Anthony Huxley, The Stockton Press, New York, pp. 237, 238, 565, 1992.

*Primary Examiner*—Howard J. Locker
*Assistant Examiner*—Anne Marie Grünberg
*Attorney, Agent, or Firm*—Michael I. Kroll

[57] ABSTRACT

A Laua'e plant which is a true dwarf cultivar, wherein the various dimensions of the plant parts are proportionally smaller, but of substantially the same color and orientation as a standard Laua'e plant.

2 Drawing Sheets

BACKGROUND OF THE INVENTION

The invention relates to a new and distinct cultivar of Laua'e named 'Laua'e Iki'. Laua'e is an ornamental fern, *Microsorium scolopendrium*, of the family Polypodiaceae. Laua'e is primarily cultivated for use as ground cover, particularly in tropical regions such as Hawai'i.

The cultivar is in fact a dwarf wherein all of the usual elements of the known, standard (wild type) Laua'e fern are present but, with the exceptions of spore clusters and roots, are on a dwarf scale. Proportionally reduced or dwarfed to about ½ to ⅔ normal size are the leaves, stems and rhizomes.

The new cultivar was discovered in a cultivated area by the inventor in Paia, Maui, as a naturally occurring mutation of unknown origin in a population of about 10,000 Laua'e plants.

The discovery was occasioned by a distinctive growth habit whereby 'Laua'e Iki' initially produces a very large number of small, juvenile, lanceolate leaves growing much closer together than is characteristic for *M. scolopendrium*. Through prolongation of the juvenile stage and more frequent leaf initiation, 'Laua'e Iki' produces about double the number of leaves (albeit smaller) as a corresponding plant of *M. scolopendrium*. For example, a 1.75" by 2.5" by 3" container may contain 30 juvenile leaves of 'Laua'e Iki' while normal *M. scolopendrium* growing from similar starting material will have but 15 leaves. The extended juvenile stage is an observed advantage for vegetative propagation as smaller leaves, rhizomes, and shorter internodes accelerate the growth sequence resulting in more plant divisions per unit of time and propagation area.

Asexual reproduction was accomplished by division of the rhizomatous rootstock at Paia. The reproduction of the variety has shown that the unique features of this new fern are stabilized and retained over eight successive generations, involving over 15,000 plants, of rhizome separation and planting. It is anticipated that other reproductive methods such as, for example, tissue culture, can also be suitably employed and are accordingly within the scope of the invention.

The cultivar 'Laua'e Iki' has been observed under many environmental and growth situations without any indication of reversion to original type or further mutation into another form. It has been cultivated in small soil plots along with regular Laua'e for over two years with each cultivar remaining true to form. Over 100,000 have been observed in various stages of growth without recognizable reversion or further mutation, indicating the 'Laua'e Iki' is genetically stable, and is neither common nor a recognized variant of the source plant, *M. scolopendrium*.

'Laua'e Iki' responds no differently than common laua'e to minor scale and aphid problems in the nursery. No other insect problems have been noted in nursery or field. No resistance or susceptibility to pathogens has been observed.

Due to its smaller size, it is expected that 'Laua'e Iki' will be greatly preferred over the standard (wild type) laua'e plant for use as ornamental ground cover.

The new fern has not been observed under all possible environmental conditions. The phenotype may vary somewhat with variations in environment such as temperature and light intensity, without, however, any variance in genotype. The following observations and comparisons describe plants grown in Paia, under conditions generally used in commercial practice.

DESCRIPTION OF THE DRAWINGS

The new variety of *Microsorium scolopendrium* is illustrated by the accompanying Figures which depict the plant by the best possible color representation using color photography and compare it to the standard variety.

DESCRIPTION OF THE PLANT

Figure 1:
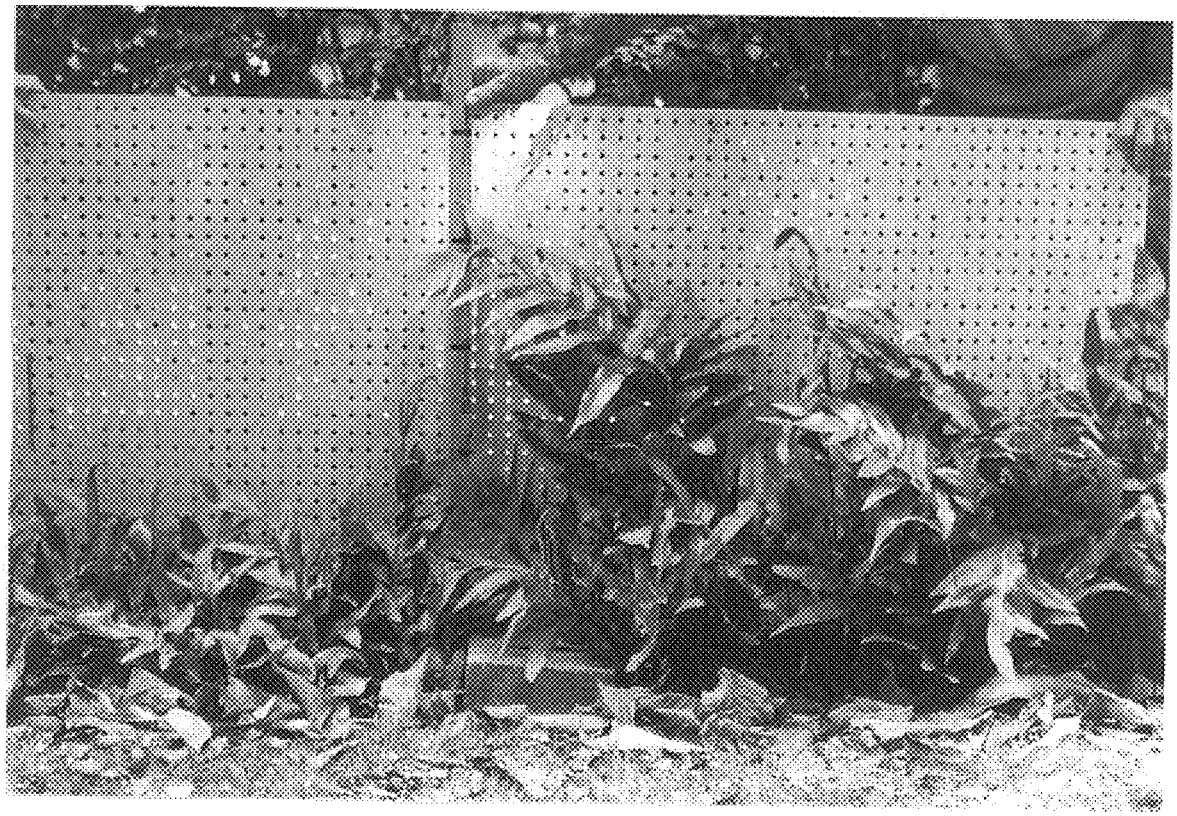
FIG. 1 illustrates the new dwarf variety (left) grown side-by-side with and under identical conditions as the standard variety (right). All plants are the same age.
Figure 2:
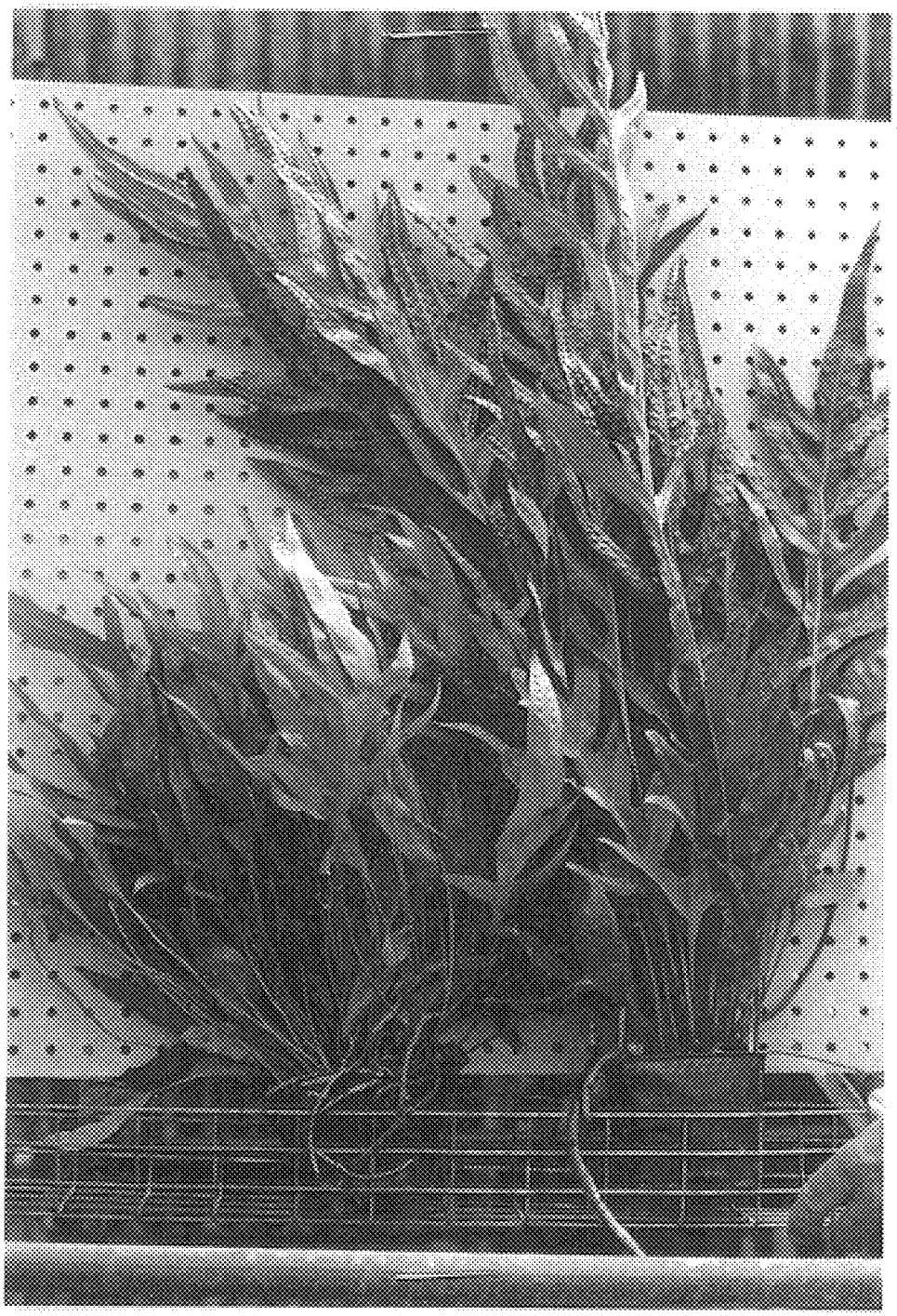
FIG. 2 also illustrates the new dwarf variety (left) grown under identical conditions as the standard variety (right), with all plants being the same age. In this depiction rhizome morphology is also illustrated.

As shown in the illustrations, the leaf color of 'Laua'e Iki' is virtually indistinguishable from the wild type. This is a very wide range of colors and does not include colors that may be obtained off the nursery benches under different nutritional or environmental conditions. Regular laua's has the same range of colors. The new fern differs from the wild-type species *Microsorium scolopendrium* in the following characteristics.

1. Plants of the new fern are more compact but retain the vigorous growth rate, growth style and overall appearance of *Microsorium scolopendrium*.

2. Rhizome thickness of the new fern is about half that of normal *Microsorium scolopendrium*, with shorter rhizome spacing between fronds.

3. Frond length and stem thickness is less, by about half, on plants of the new fern relative to that of the species *Microsorium scolopendrium*.

4. Because of the difference in size and scale, equal growth rate in terms of new but smaller leaves results in a smaller plant and a slower rate of close-in. Most importantly, this translates into a lower height at any given stage of growth with mature height being only about half to two thirds that of normal *Microsorium scolopendrium*.

5. The smaller size of this new fern combined with its vigorous growth rate greatly increases the productivity in terms of plants per unit area of nursery space, an important consideration for commercial use.

As described herein and as illustrated in the drawing figures, the new fern of the present invention is a true dwarf variety of the species *Microsorium scolopendrium*, known informally as Laua'e. The botanical classification for the new fern is *Microsorium scolopendrium* cultivar 'Laua'e Iki'. The new cultivar was discovered as a very rare mutation growing from otherwise normal rhizomes (runners).

Standard *Microsorium scolopendrium* grows to a height of three to four feet. For use as ornamental ground cover, however, a maximum adult height about half that (from about 18 to 24 inches) would be much more preferred. The new dwarf variety exhibits, under identical growing conditions, a growth rate and maximum size about half normal. For example, the drawings illustrate both dwarf and normal plants of the same age, about five months. The average height of the normal plants is about 26 inches, while the average height of the dwarf plant is about 14 inches. This difference is growth rate and ultimate plant size has been identified throughout the life cycle of the dwarf. While the rhizomes and fronds of the plant appear to be proportionally smaller in the new variety, the other morphological aspects appear identical, for example, color, shape, location and appearance of sori, etc.

Botanical classification: *Microsortium scolopendrium* cultivar 'Laua'e Iki.'
Parentage: Naturally occurring sport or mutation of the species *Microsorium scolopendria* (Laua'e fern).
Origin: Mutation.
Form: Herbaceous.
Propagation: Rhizome separation.
Rooting habit: Rhizomes are creeping and fibrous.
Height: Average 12 to 18 inches, maximum observed height 24 inches.
Leaves: One (1) per stem, simple, usually lobed.
Stems: 2 to 12 inches.
Foliage: Irregularly lobed in shape, one rachis per frond.
Leaf: 5 to 12 inches in length, 1 to 6 inches in width.

Chart A compares characteristics of 'Laua'e Iki' and *M. scolopendrium* against each other after cultivation under very similar conditions in four adjacent and alternating plots. Each of these, in turn, may be compared against an accepted description of *M. scolopendrium* (right column) copied from page 238 of The New Royal Horticultural Society Directory of Gardening.

CHART A

| | COMPARATIVE OBSERVATIONS | |
|---|---|---|
| CHARACTERISTIC | LAUA'E IKI | *M. Scolopendrium* |
| RHIZOME | | |
| HABIT | long-creeping, fleshy | long-creeping, fleshy |
| WIDTH | to 1 cm | to 1 cm |
| COLOR | green to brown | green to brown |
| SCALES | to 4 mm caducous, ovate to lanceolate or deltoid, apex narrowly acute, clathrate, dark brown | to 5 mm caducous, ovate to lanceolate or deltoid, apex narrowly acute, clathrate, dark brown |
| FRONDS | to 28 × 18 cm, deeply pinnatifid, oblong to ovate, base attenuate and decurrent, or rarely, simple, lanceolate, smaller, leathery to papery, glabrous, lustrous, lt. green, seg. to 12 × 2.5 cm, opposite to rarely alternate, to 5 pairs, spreading lanceolate to linear, oblong, or strap-shaped, apex narrowly acute to obtuse, margin entire to thickened and somewhat falcate, terminal seg. Elongate | to 53 × 27 cm, deeply pinnatifid, oblong to ovate, base attenuate and decurrent, or rarely, simple, lanceolate, smaller, leathery to papery, glabrous, lustrous, lt. green, seg. to 18 × 3 cm, opposite to rarely alternate, to 8 pairs, spreading lanceolate to linear, oblong, or strap-shaped, apex narrowly acute to obtuse, margin entire to thickened and somewhat falcate, terminal seg. Elongate |
| STIPES | to 30 cm, 10 cm distant, glabrous, lustrous, stamineous | |
| ROOTS | .5 mm | .5 mm |
| SPOROPHORE | 4 mm, orange–tan | 4 mm, orange–tan |
| SORI | 2 mm, orange–tan | 2 mm, orange–tan |

| CHARACTERISTIC | T.N.R.H.S.D.O.G. *M. scolopendrium* |
|---|---|
| RHIZOME | |
| HABIT | long-creeping, fleshy |
| WIDTH | to 1 cm |
| COLOR | green to brown |
| SCALES | to 5 mm caducous, ovate to lanceolate or deltoid, apex narrowly acute, clathrate, dark brown |
| FRONDS | to 40 × 30 cm, deeply pinnatifid, oblong to ovate, base attenuate and decurrent, or rarely, simple, lanceolate, smaller, leathery to papery, glabrous, lustrous, lt. green, seg. to 15 × 3 cm, opposite, to 5 pairs, spreading lanceolate to linear, oblong, or strap-shaped, apex narrowly acute to obtuse, margin entire to thickened and somewhat falcate, terminal seg. Elongate |
| STIPES | to 30 cm, 8 cm distant, glabrous, lustrous, stamineous |

CHART A-continued

| |
|---|
| ROOTS |
| SPOROPHORE |
| SORI |

It will be noted from Chart A that the distinguishing, mature characteristics of 'Laua'e Iki' are: reduction in rhizome diameter, reduction in size of fronds and pinnatifid pairs, reduction of stipe length, and reduction of height when compared under similar or identical growing conditions. Color is not a distinguishing factor as both 'Laua'e Iki' and *M. scolopendrium* exhibit similar if not identical ranges of green leaf color that vary widely with nutrition, light intensity and possibly other factor. Colors of sporophores, spores, and other parts of the plants are also indistinguishable between the two cultivars when grown under similar conditions.

A distinguishing feature of 'Laua'e Iki' is its juvenile tendency to produce about double the number of juvenile lanceolate fronds that are about ½ to ¾ the size of those produced by *M. scolopendrium* growing under the same conditions. This juvenile tendency of 'Laua'e Iki' persists after similar plants of *M. colopendrium* have moved into the adult stage with the production of deeply pinnatifid leaves.

Using the Pantone Book of Color, 'Laua'e Iki' leaf colors could be matched to PANTONE 19-0323 through 16-0532 with many shades in between, and possibly some beyond. This is a very wide range of colors and does not include colors that may be obtained off the nursery benches under different nutritional or environmental conditions. Regular laua'e has the same range of colors.

What is claimed as new and desired to be protected by Letters Patent is set forth in the appended claims:

1. A dwarf Laua'e plant, substantially as herein shown and described, characterized particularly by its proportionally dwarfed dimensions as compared with a standard Laua'e plant.

* * * * *